United States Patent
Stevens

(10) Patent No.: US 6,200,374 B1
(45) Date of Patent: Mar. 13, 2001

(54) ANTI-BACTERIAL LIQUID BINDER FOR USE AS A PRE-APPLICATION BINDER WITH COSMETIC POWDERS FOR EYE LINERS, EYE SHADOWS AND EYEBROW MAKEUP AND THE METHOD FOR MAKING SAME

(76) Inventor: Richard Stevens, 2650 Avon, Newport Beach, CA (US) 92663

( * ) Notice: Subject to any disclaimer, the term of this patent is extended or adjusted under 35 U.S.C. 154(b) by 0 days.

(21) Appl. No.: 09/389,901

(22) Filed: Sep. 3, 1999

(51) Int. Cl.$^7$ ........................................ A61K 7/02
(52) U.S. Cl. ................. 106/217.7; 514/777; 514/844
(58) Field of Search .................. 106/217.7; 514/777, 514/844; 424/401, 532

(56) References Cited

U.S. PATENT DOCUMENTS 5,965,145 * 10/1999 Marion et al. ................ 424/401

* cited by examiner

*Primary Examiner*—David Brunsman
(74) *Attorney, Agent, or Firm*—Ben E. Lofstedt, Patent Attorney

(57) ABSTRACT

An improved antibacterial liquid binder for use as a pre-application binder with cosmetic powders for eye liners, eye shadows and eyebrow makeup including a unique blended mixture of de-ionized water, honey, isopropyl alcohol, potassium alum, propylene glycol, boric acid, and methylparaben, and, more specifically, a new and novel admixture and combination of these ingredients, by weight, as follows: deionized water—70.97%, honey—20.88%, isopropyl alcohol—5.25%, potassium alum—0.9%, propylene glycol—0.9%, boric acid—0.9%, and methylparaben—0.2%. The method for making such improved liquid binder for pre-application combination with cosmetic powders, eye shadows and eyebrow makeup including the steps of adding the potassium alum to the isopropyl alcohol and mixing the combined potassium alum and isopropyl alcohol to form a homogenous solution, adding the boric acid to the combination of potassium alum and isopropyl alcohol and mixing the combined boric acid, potassium alum and isopropyl alcohol to form a homogenous solution, mixing the methylparaben with the propylene glycol to form a homogenous solution, pre-heating the combined liquid solution formed by the mixing of methylparaben with the propylene glycol until the combined liquid solution is homogenous, clear and transparent, pre-heating the honey to reduce the viscosity of the honey, adding the pre-heated homogenous, clear and transparent liquid solution formed of the mixture of methylparaben and propylene glycol to the pre-heated honey, mixing the mixture of methylparaben and propylene glycol with the pre-heated honey to form a homogenous solution, pouring the combination of methylparaben, propylene glycol, honey, isopropyl alcohol, potassium alum, and boric acid into the deionized water and mixing the combination formed thereby to form a homogenous solution.

2 Claims, No Drawings

ANTI-BACTERIAL LIQUID BINDER FOR USE AS A PRE-APPLICATION BINDER WITH COSMETIC POWDERS FOR EYE LINERS, EYE SHADOWS AND EYEBROW MAKEUP AND THE METHOD FOR MAKING SAME

BACKGROUND OF THE INVENTION

1. Field of the Invention

This invention relates to an improved antibacterial liquid binder for use as a pre-application binder for cosmetic powders applied on the facial skin of a human being, and, more specifically, to an improved liquid binder for use as a pre-application binder for cosmetics such as eye liners, eye shadows and eyebrow makeup and the method for making such improved liquid binder 2. Description of the Prior Art Cosmetic powders used for adorning the face and areas about the face must be formulated of very fine powders in order to properly color and blend in with the nature skin color.

If the cosmetic powders are not fine enough, a close-up, natural unaided, and unmagnified view through the eyes of another person standing in close proximity to the facial skin covered with such cosmetic powders will not appear to be smooth and/or natural. It is, therefore, important for the cosmetic powders to be ground to a very fine powder form in order to be considered as acceptable for use as a cosmetic powder suitable for covering the skin on the face of a person.

One of the problems associated with the use of such fineness of these cosmetic powders for covering skin discolorations and surface blemishes is such that these facial cosmetic powders are unable to adhere very well to the surface of the skin following deposition thereon. Deposition of such fine cosmetic powders is typically by the use of a very fine brush. Oftentimes, such brushes are constructed of very fine and soft camel's hair.

Facial cosmetic powders must be ground to such a degree of fineness that the powders will not "cake up" or contain any cosmetic powders which have a tendency to "lump up" together. Such "caking" or "lumping" up, is a highly undesirable cosmetic powders because such characteristics in cosmetic powders or lumpy as such creates surfaces undulations on top of the skin. Such surface undulations create shadows over the skin's surface and cause the skin's surface to be rough in texture. Finely ground cosmetic powders and cosmetic powders which do not "cake" or "lump" up are, in fact, a virtual requirement for use in facial cosmetic applications. And, this is especially the case for use around the eyes where fine creases form as folds in the skin as a person ages and the skin looses some of its elasticity and begins to sag.

However, the use of such fine powder for covering facial skin blemishes and discolorations presents another significant problem: exfoliation due to lack of adequate adherence to the skin. In the use of such fine cosmetic powders, it has been found that when such fine powders are applied over the surface of the skin, that the natural skin oils tend to lift such very finely ground cosmetic powders from the surface of the skin causing such powders, and, hence, the colored cosmetic powders, to be displaced and fall off the skin. Or, even worse yet, to "run" from the facial area where the cosmetic powders were initially placed and blended in with a very fine brush to another area of the face. Such movement or displacement is highly undesirable and often embarrassing for the person whose face is adorned with such fine cosmetic powders caused by the resulting blotchy appearance over the facial skin due to the lifting, peeling and/or lateral migration of the cosmetic powder from the area of the face where it was initially brushed on by the skillful artistry of a cosmetologist to another part of the facial skin.

Additionally, various fine cosmetic quality powders are used in high-quality admixtures for the tender skin about the eyes, the eyebrows, the eyelashes, and similar facial skin areas. However, with each flash or rapid movement of the eyelashes, or skin wrinkling causes by a smile or laugh, the cosmetic powders tend to become quickly lifted or disassociated from the facial skin area to which the cosmetic powder was applied. Eyebrow movement also produces the lift or separation between the fine cosmetic powders and the soft skin covering the face. Consequently, as a result of the disassociation of these very fine cosmetic powders, the cosmetic powders must be frequently and carefully reapplied during the course of an evening out on the town, so to speak.

This difficult problem has been greatly overcome by the use of a new and novel admixture and combination of the following ingredients, by weight:

1. De-ionized water—70.97%
2. Honey—20.88%
3. Isopropyl alcohol—5.25%
4. Potassium alum—0.9%
5. Propylene glycol—0.9%
6. Boric acid—0.9%
7. Methylparaben—0.2%

Further, the method for making such improved liquid binder for pre-application combination with cosmetic powders, eye shadows and eyebrow makeup including the steps of adding the potassium alum to the isopropyl alcohol and mixing the combined potassium alum and isopropyl alcohol to form a homogenous solution, adding the boric acid to the combination of potassium alum and isopropyl alcohol and mixing the combined boric acid, potassium alum and isopropyl alcohol to form a homogenous solution, mixing the methylparaben with the propylene glycol to form a homogenous solution, pre-heating the combined liquid solution formed by the mixing of methylparaben with the propylene glycol until the combined liquid solution is homogenous, clear and transparent, pre-heating the honey to reduce the viscosity of the honey, adding the pre-heated homogenous, clear and transparent liquid solution formed of the mixture of methylparaben and propylene glycol to the pre-heated honey, mixing the mixture of methylparaben and propylene glycol with the pre-heated honey to form a homogenous solution, pouring the combination of methylparaben, propylene glycol, honey, isopropyl alcohol, potassium alum, and boric acid into the deionized water and mixing the combination formed thereby to form a homogenous solution.

As the inventor, I have chosen to refer to this combination of ingredients Sticky Stuff. Sticky Stuff solves the many problems and difficulties associated in the prior art use of finely cosmetic facial powders. Sticky Stuff is used as a solution as follows:

1. To allow a person (usually a woman) to apply an eyebrow powder brow color with greater ease;
2. To increase and improve and lengthen the staying power of the combination relative to the facial skin and hair to which it is applied;
3. To enhance and to create a much more natural look than ever seen before;

4. A single drop of Sticky Stuff applied to a fine cosmetic facial brush allows the user of the cosmetic powder combination created thereby to experience an ease of application and lasting power unlike any other previously used product on the market.

5. Additionally, because the use of Sticky Stuff makes the cosmetic brush stiffer, the person applying the combination of the cosmetic powder and Sticky Stuff, that person has a greater degree of control in the application to the face, facial areas and facial hairs than ever before found in the prior art;

6. Further, Sticky Stuff and the cosmetic powder forms a combination product that will stay on until the user decides to remove the cosmetic facial combination from his or her face or hair; and 7. The combination formed by Sticky Stuff and the cosmetic powder produces a product that now makes it possible to make eyeshadow adhere to the fine, tender and sensitive skin about the human eye better than any of the conventional methods that are available on the market.

U.S. Pat. No. 4,506,044 (Cox, et al.) describes a novel heteropolysaccharide and a process for producing it by bacterial fermentation of an aqueous nutrient medium, and to an organism which produces the heteropolysaccharide. Polysaccharides have been employed as thickeners or suspending agents, particularly in water-based systems such as foods, cosmetics and pharmaceuticals.

U.S. Pat. No. 5,073,545 (Arima et al.) relates to an agent containing an ellagic acid series compound for external application and use thereof. Basically, this is an agent for external application such as cosmetics that are excellent in stability and safety and give a skin lightening and whitening effect. While de-ionized water is not specifically mentioned, the use of "purified water" is. De-ionized water is purified water which is de-ionized. Neither the use of potassium alum or honey is mentioned. However, the use of isopropyl alcohol, propylene glycol, boric acid, and methylparaben is mentioned.

U.S. Pat. No. 5,308,896 (Hansen, et al.) relates to particle binders for high bulk fibers. This patent contains information and disclosures similar to those contained in U.S. Pat. No. 5,547,541 (Hansen, et al.) and in U.S. Pat. No. 5,547,745 which is also issued to Hansen.

U.S. Pat. No. 5,409,703 (McAnalley, et al) describes a therapeutic medical device comprised of a dried hydrogel of a hydrophilic-hygroscopic polymer, such as an unmodified or modified polymeric carbohydrate, in the form of a solid foam. The described therapeutic device can serve as a dressing for a wound or lesion, drug delivery system, a hemostatic agent and a biologic response modifier.

U.S. Pat. No. 5,447,977 (Hansen, et al.) describes a method for producing easily densified high bulk fibers that have adhered particulates. This patent contains information similar to that contained in U.S. Pat. No. 5,547,541 (Hansen, et al.) and U.S. Pat. No. 5,547,745 which is also issued to Hansen.

U.S. Pat. No. 5,547,541 (Hansen, et al.) discloses a method for densifying fibers using a densifying agent. This patent contains information similar to U.S. Pat. No. 5,547,745 which is also issued to Hansen.

U.S. Pat. No. 5,547,745 (Hansen) relates to particle binders. Specifically, it concerns polymeric and non-polymeric binders for fibers and the use of such binders in binding particles to fibers. One of the applications and uses of this particular invention relates to binding superabsorbent particles to cellulosic fibers which may then be used, for example, to make absorbent fibers that are densified and incorporated in to absorbent products. This invention primarily is found to be useful to increase the absorbency of sanitary products such as diapers and sanitary napkins.

U.S. Pat. No. 5,538,728 (Yanaki, et al.) relates to hydrophilic polymer-silicate mineral complex material and use thereof. Basically, a material is described having a very high water retentivity which is swelled and gelled by absorption of an aqueous substance to an extremely high degree which in contact with the aqueous substance, and further, the gel-like aromatic compositions, and cosmetics.

While some of the above patents mention the use of a combination similar to Sticky Stuff it is noted that none discuss the same or similar unique combination and product and its formation, combination and use with cosmetic powders as disclosed herein or the use of the combination of cosmetic powders for the use and application created herein.

SUMMARY OF THE INVENTION AND OBJECTS

Basically, the present invention is described as an improved antibacterial liquid binder for cosmetic powders for eye liners, eye shadows and eyebrow makeup including a mixture of de-ionized water, honey, isopropyl alcohol, potassium alum, propylene glycol, boric acid, and methylparaben in combination, by volume and weight, as follows:

| Element | % of Element By Weight |
| --- | --- |
| De-ionized water | 70.97 |
| Honey | 20.88 |
| Isopropyl alcohol | 5.25 |
| Potassium alum | 0.90 |
| Propylene glycol | 0.90 |
| Boric acid powder | 0.90 |
| Methylparaben | 0.20 |

The process of forming Sticky Stuff by combining the aforementioned, above-referenced elements, by weight for making such improved liquid binder for pre-application combination with cosmetic powders, eye shadows and eyebrow makeup including the steps of adding the potassium alum to the isopropyl alcohol and mixing the combined potassium alum and isopropyl alcohol to form a homogenous solution, adding the boric acid to the combination of potassium alum and isopropyl alcohol and mixing the combined boric acid, potassium alum and isopropyl alcohol to form a homogenous solution, mixing the methylparaben with the propylene glycol to form a homogenous solution, pre-heating the combined liquid solution formed by the mixing of methylparaben with the propylene glycol until the combined liquid solution is homogenous, clear and transparent, pre-heating the honey to reduce the viscosity of the honey, adding the pre-heated homogenous, clear and transparent liquid solution formed of the mixture of methylparaben and propylene glycol to the pre-heated honey, mixing the mixture of methylparaben and propylene glycol with the pre-heated honey to form a homogenous solution, pouring the combination of methylparaben, propylene glycol, honey, isopropyl alcohol, potassium alum, and boric acid into the deionized water and mixing the combination formed thereby to form a homogenous solution.

It is one important and significant object of the invention herein to create a most useful combination of cosmetic powders with the admixture of elements known as Sticky Stuff It is a yet still further unique and important object and feature of the within described invention that the process, sequence and steps taken to form this new and unique material known as Sticky Stuff is in itself believed to be new and novel.

Another significant and primary object of the invention herein is to adhesively adhere the combination of very fine cosmetic powders into a product which will comfortably adhere to the skin of the user.

A still further and significant object and feature of the instant invention described and disclosed herein is to provide a product which can be used in combination with ultra-finely ground cosmetic powders to create a longer residual adherence time on the skin of the user, especial in the facial area.

A yet still further important and primary object of the invention is to create a new product which allows for greatly enhanced control of the application of the combination Sticky Stuff and the fine cosmetic powders.

Yet another primary and important object of the invention disclosed herein as Sticky Stuff is to create an enhanced ease of use with respect to the application of the combination of Sticky Stuff and very fine cosmetic powders to the face and facial hairs.

A yet still further and important feature of the present invention is to form a pre-application cosmetic binder which is antibacterial in character to prevent skin and eye infections caused by the use of cosmetics and cosmetic powders applied to the face and about the eyes.

The foregoing and other features and advantages of the invention will become more apparent form the following detailed description.

DESCRIPTION OF THE PREFERRED EMBODIMENT OF THE INVENTION

The present invention, in summary, comprises an improved liquid binder for cosmetic powders for eye liners, eye shadows and eyebrow makeup including a mixture of de-ionized water, honey, isopropyl alcohol, potassium alum, propylene glycol, boric acid, and methylparaben, and the method and process for combining such ingredients to create such a liquid binder.

Disclosed and described in detail herein is a new and unique and improved antibacterial liquid binder for use as a pre-application binder with cosmetic powders for eye liners, eye shadows and eyebrow makeup including a unique blended mixture of de-ionized water, honey, isopropyl alcohol, potassium alum, propylene glycol, boric acid, and methylparaben.

Additionally, to make such new and novel improved antibacterial liquid binder, a new and novel method has been created for producing such improved liquid binder for pre-application combination with cosmetic powders, eye shadows and eyebrow makeup including the steps of adding the potassium alum to the isopropyl alcohol and mixing the combined potassium alum and isopropyl alcohol to form a homogenous solution, adding the boric acid to the combination of potassium alum and isopropyl alcohol and mixing the combined boric acid, potassium alum and isopropyl alcohol to form a homogenous solution, mixing the methylparaben with the propylene glycol to form a homogenous solution, pre-heating the combined liquid solution formed by the mixing of methylparaben with the propylene glycol until the combined liquid solution is homogenous, clear and transparent, pre-heating the honey to reduce the viscosity of the honey, adding the pre-heated homogenous, clear and transparent liquid solution formed of the mixture of methylparaben and propylene glycol to the pre-heated honey, mixing the mixture of methylparaben and propylene glycol with the pre-heated honey to form a homogenous solution, pouring the combination of methylparaben, propylene glycol, honey, isopropyl alcohol, potassium alum, and boric acid into the deionized water and mixing the combination formed thereby to form a homogenous solution.

I prefer to call this new and unique cosmetic product "Sticky Stuff."

The Combination of Ingredients in "Sticky Stuff"

This unique product "Sticky Stuff" is formed from the following ingredients, by weight:

Percentage by Weight

The percentages of the total by weight of this special admixture combination preferred to form "Sticky Stuff" are as follows:

| Percentage of Total by Weight | Description of Elements |
| --- | --- |
| 70.97% | De-ionized water |
| 20.88% | Honey |
| 5.25% | Isopropyl alcohol |
| 0.90% | Potassium alum |
| 0.90% | Propylene glycol |
| 0.90% | Boric acid |
| 0.20% | Methylparaben |

DESCRIPTION OF ELEMENTAL CHEMICAL BACKGROUND

Alum is any of a group of chemical compounds, made up of water molecules and two kinds of salts, one of which is usually aluminum sulfate ($Al_2(SO_4)_3$), combined in definite proportions. Potassium alum, also known as common alum, has the chemical formula $K_2SO_4.Al_2(SO_4)_3.24H_2O$. Potassium alum is a powerful astringent. Potassium alum is the most important type of alum. Potassium alum is created by dissolving potassium sulfate and aluminum sulfate together, then cooling the resulting solution to form a colorless substance that forms large octahedral or cubic crystals. Potassium alum solutions are acidic. Potassium alum is soluble in seven times its weight of water at room temperature and is very soluble in hot water. When crystalline potassium alum is heated, some of the water of hydration becomes chemically separated, and the partly dehydrated salt dissolves in this water, with the resulting appearance that the alum appears to melt at about 90° C. (about 194° F.). An astringent such as alum closes the openings of the sweat glands in the skin. Any substance that is used medicinally or industrially to contract tissues and reduce mucus and other secretions is said to be astringent. Solutions of mineral salts are usually astringent.

Boric acid as described and referenced herein is in powder rather than aqueous form. Boric acid is recognized and known for its astringent and antiseptic properties. Boric acid also has orbitals empty in its electron shell structure which is available for coordinate covalent bonding in a chemical reaction with another substance having a pair of electrons with donor capability. The boron atom of boric acid is an acceptor for a lone pair of electrons donated by an oxygen atom of polypropylene glycol (PPG), thereby forming a coordinate covalent bond between a boric acid particle and polypropylene glycol binder. Boric acid functions as a surfactant with other liquids such as water or solvents. It surfactant qualities assist in its function as a binder with the fiber-like qualities of the finely ground cosmetics powders.

The potassium coordinate covalently bonded in an aluminum matrix compound is characterized as aluminum trihydrate which may participate in a coordinate covalent bond with polypropylene glycol which is a polymer. In this chemical interaction, the aluminum atom of aluminum trihydrate acts as an electron acceptor for an electron pair donated by an oxygen atom of the polypropylene glycol binder.

Isopropyl alcohol is an astringent and an antibacterial solvent which functions to kill any active bacteria harbored in the finely ground cosmetic powders, and any of the other ingredients described herein. It is also described as a topical antiseptic. Isopropyl alcohol is antiprotozoal to kill any Giardia bacteria that may be growing in the de-ionized water to prevent an outbreak of Giardia-caused intestinal infections due to ingestation of the combination of materials formed by the new and unique interfunctioning combinations herein described.

It should be noted, at this time, that the combination product described herein, when formed, and thereafterwards combined with the finely ground cosmetic powders, acts and functions as a cosmetic preservative, and a topical antibacterial and anti-infective for the user of the pre-application cosmetics binder disclosed and described herein.

Having illustrated and described the principles of the invention in the above-identified preferred embodiment of the invention, it should be apparent to those skilled in the art that the invention can be modified in arrangement and detail without departing from such principles. I claim all modifications coming within the spirit and scope of the following claims.

I claim:

1. An improved liquid binder for use as a pre-application binder for cosmetic powders for application and use on the face for eye liners, eye shadows, eyebrow makeup, and the like, including a mixture of the following proporsions by weight:
   (a) 70–97% de-ionized water;
   (b) 20–88% honey;
   (c) 5–25% isopropyl alcohol;
   (d) 0–90% potassium alum;
   (e) 0–90% propylene glycol;
   (f) 0–90% boric acid; and
   (g) 0–20% methylparaben.

2. The method for making the improved liquid binder of claim 1 for pre-application combination with cosmetic powders for eye liners, eye shadows, eyebrow makeup, and the like, comprising the steps of: adding the potassium alum to the isopropyl alcohol and mixing the combination of potassium alum and isopropyl alcohol to form a homogenous solution, adding the boric acid to the combination of potassium alum and isopropyl alcohol and mixing the combination of boric acid, potassium alum and isopropyl alcohol to form a homogenous solution, mixing the methylparaben with the propylene glycol to form a homogenous solution, pre-heating the combined liquid solution formed by the mixing of methylparaben with the propylene glycol until the combined liquid solution is homogenous, clear and transparent, pre-heating the honey to reduce the viscosity of the honey, adding the pre-heated homogenous, clear and transparent liquid solution formed of the mixture of methylparaben and propylene glycol to the pre-heated honey, mixing the mixture of methylparaben and propylene glycol with the pre-heated honey to form a homogenous solution, pouring the combination of methylparaben, propylene glycol, honey, isopropyl alcohol, potassium alum, and boric acid into the deionized water and mixing the combination formed thereby to form a homogenous solution.

* * * * *